US007013176B2

(12) United States Patent
Ding et al.

(10) Patent No.: US 7,013,176 B2
(45) Date of Patent: Mar. 14, 2006

(54) METHOD AND APPARATUS FOR SETTING PACING PARAMETERS IN CARDIAC RESYNCHRONIZATION THERAPY

(75) Inventors: Jiang Ding, Maplewood, MN (US); Yinghong Yu, Maplewood, MN (US); Andrew P. Kramer, Stillwater, MN (US); Lawrence Baumann, Bloomington, MN (US)

(73) Assignee: Cardiac Pacemakers, Inc., Saint Paul, MN (US)

( * ) Notice: Subject to any disclaimer, the term of this patent is extended or adjusted under 35 U.S.C. 154(b) by 504 days.

(21) Appl. No.: 10/352,780

(22) Filed: Jan. 28, 2003

(65) Prior Publication Data

US 2004/0147966 A1    Jul. 29, 2004

(51) Int. Cl.
*A61N 1/365*    (2006.01)
(52) U.S. Cl. ........................................................ 607/9
(58) Field of Classification Search ............... 607/4–28
See application file for complete search history.

(56) References Cited

U.S. PATENT DOCUMENTS

| | | | |
|---|---|---|---|
| 4,401,119 A | 8/1983 | Herpers | 607/9 |
| 4,432,362 A | 2/1984 | Leckrone et al. | 607/9 |
| 4,922,907 A | 5/1990 | Hedin et al. | 128/419 P |
| 5,312,452 A | 5/1994 | Salo | 607/17 |
| 5,318,595 A | 6/1994 | Ferek-Petric et al. | 607/17 |
| 5,330,511 A | 7/1994 | Boute | 607/25 |
| 5,334,222 A | 8/1994 | Salo et al. | 607/17 |
| 5,372,607 A | 12/1994 | Stone et al. | 607/30 |
| 5,413,592 A | 5/1995 | Schroeppel | 607/18 |
| 5,417,717 A | 5/1995 | Salo et al. | 607/18 |
| 5,466,245 A | 11/1995 | Spinelli et al. | 607/17 |
| 5,487,752 A | 1/1996 | Salo et al. | 607/17 |
| 5,514,163 A | 5/1996 | Markowitz et al. | 607/9 |
| 5,527,347 A | 6/1996 | Shelton et al. | 607/9 |
| 5,534,016 A | 7/1996 | Boute | 607/9 |
| 5,540,727 A | 7/1996 | Tockman et al. | 607/18 |
| 5,549,650 A | 8/1996 | Bornzin et al. | 607/24 |
| 5,584,868 A | 12/1996 | Salo et al. | 607/17 |
| 5,609,612 A | 3/1997 | Plicchi et al. | 607/17 |
| 5,626,620 A | 5/1997 | Kieval et al. | 607/9 |
| 5,626,623 A | 5/1997 | Kieval et al. | 607/23 |
| 5,628,777 A | 5/1997 | Moberg et al. | 607/122 |
| 5,690,689 A | 11/1997 | Sholder | 607/24 |
| 5,713,930 A | 2/1998 | van der Veen et al. | 607/25 |
| 5,716,383 A | 2/1998 | Kieval et al. | 607/9 |
| 5,749,906 A | 5/1998 | Kieval et al. | 607/9 |
| 5,800,471 A | 9/1998 | Baumann | 607/25 |
| 5,836,987 A | 11/1998 | Baumann et al. | 607/17 |

(Continued)

FOREIGN PATENT DOCUMENTS

EP        0970721 A2    1/2000

(Continued)

OTHER PUBLICATIONS

Partial International Search Report in PCT/US2004/002332.

(Continued)

*Primary Examiner*—Scott M. Getzow
(74) *Attorney, Agent, or Firm*—Schwegman, Lundberg, Woessner & Kluth, P.A.

(57) ABSTRACT

A method and apparatus is disclosed for automatically setting the pacing parameters utilized by an implantable cardiac device in delivering cardiac resynchronization therapy. The selection of the pacing parameters is based at least in part upon measurements of intrinsic cardiac conduction parameters. Among the pacing parameters which may be selected in this way is the atrio-ventricular delay interval used in atrial-tracking and AV sequential pacing modes.

31 Claims, 7 Drawing Sheets

U.S. PATENT DOCUMENTS

| | | | |
|---|---|---|---|
| 5,891,176 A | 4/1999 | Bornzin | 607/18 |
| 6,144,880 A | 11/2000 | Ding et al. | 607/23 |
| 6,208,901 B1 | 3/2001 | Hartung | 607/23 |
| 6,280,389 B1 | 8/2001 | Ding et al. | 600/485 |
| 6,351,673 B1 | 2/2002 | Ding et al. | 607/24 |
| 6,360,127 B1 | 3/2002 | Ding et al. | 607/23 |
| 6,430,439 B1 | 8/2002 | Wentkowski et al. | 607/9 |
| 6,438,421 B1 | 8/2002 | Stahmann et al. | 607/9 |
| 6,449,510 B1 | 9/2002 | Albers et al. | 607/25 |
| 6,480,742 B1 | 11/2002 | Stahmann et al. | 607/27 |
| 6,507,756 B1 | 1/2003 | Heynen et al. | 607/9 |
| 6,512,952 B1 | 1/2003 | Stahmann et al. | 607/9 |
| 6,522,921 B1 | 2/2003 | Stahmann et al. | 607/9 |
| 6,522,923 B1 | 2/2003 | Turcott | 607/27 |
| 6,542,775 B1 | 4/2003 | Ding et al. | 607/24 |
| 6,553,258 B1 | 4/2003 | Stahmann et al. | 607/9 |
| 6,597,951 B1 | 7/2003 | Kramer et al. | 607/9 |
| 6,684,103 B1 | 1/2004 | Ding et al. | 607/23 |
| 2001/0047194 A1 | 11/2001 | Thompson et al. | 607/59 |
| 2002/0123769 A1 | 9/2002 | Panken et al. | 607/9 |
| 2002/0183795 A1 | 12/2002 | Rouw et al. | 607/9 |
| 2003/0097158 A1 | 5/2003 | Belalcazer | 607/32 |
| 2003/0105496 A1 | 6/2003 | Yu et al. | 607/17 |
| 2003/0144702 A1 | 7/2003 | Yu et al. | 607/17 |
| 2003/0144703 A1 | 7/2003 | Yu et al. | 607/17 |
| 2004/0019365 A1 | 1/2004 | Ding et al. | 607/17 |
| 2004/0078059 A1 | 4/2004 | Ding et al. | 607/25 |
| 2004/0078060 A1 | 4/2004 | Ding et al. | 607/25 |

FOREIGN PATENT DOCUMENTS

| | | |
|---|---|---|
| WO | WO-99/58191 A1 | 11/1999 |
| WO | WO-2004/011088 A1 | 2/2004 |
| WO | WO-2004/069333 A2 | 8/2004 |

OTHER PUBLICATIONS

Kramer, A. P., et al., "Method and Apparatus for Adjustment of Sequential Biventricular Pacing", U.S. Appl. No. 10/742,630, filed Dec. 19, 2003, 41 Pages.

Kramer, A. P., et al., "Automatic Selection From Multiple Cardiac Optimization Protocols", U.S. Appl. No. 10/624,458, filed Jul. 21, 2003, 49 pages.

Ritter, P., et al., "A Built-In System Based on the Peak Endocardial Acceleration (PEA) for AV-Delay Optimization in DDDR Pacing", *Pace—Pacing and Clinical Electrophysiology*, No. 5, Futura Publishing Company, Inc.,(May 1997), 1567.

FIG. 7

METHOD AND APPARATUS FOR SETTING PACING PARAMETERS IN CARDIAC RESYNCHRONIZATION THERAPY

FIELD OF THE INVENTION

This invention pertains to cardiac rhythm management devices such as pacemakers and other implantable devices for treating cardiac dysfunction.

BACKGROUND

Cardiac rhythm management devices are implantable devices that provide electrical stimulation to selected chambers of the heart in order to treat disorders of cardiac rhythm. A pacemaker, for example, is a cardiac rhythm management device that paces the heart with timed pacing pulses. The most common condition for which pacemakers are used is in the treatment of bradycardia, where the ventricular rate is too slow. Atrio-ventricular conduction defects (i.e., AV block) that are permanent or intermittent and sick sinus syndrome represent the most common causes of bradycardia for which permanent pacing may be indicated. If functioning properly, the pacemaker makes up for the heart's inability to pace itself at an appropriate rhythm in order to meet metabolic demand by enforcing a minimum heart rate and/or artificially restoring AV conduction.

Pacing therapy can also be used in the treatment of heart failure, which refers to a clinical syndrome in which an abnormality of cardiac function causes a below normal cardiac output that can fall below a level adequate to meet the metabolic demand of peripheral tissues. When uncompensated, it usually presents as congestive heart failure due to the accompanying venous and pulmonary congestion. Heart failure can be due to a variety of etiologies with ischemic heart disease being the most common. It has been shown that some heart failure patients suffer from intraventricular and/or interventricular conduction defects (e.g., bundle branch blocks) such that their cardiac outputs can be increased by improving the synchronization of ventricular contractions with electrical stimulation. Other conduction defects can occur in the atria. Cardiac rhythm management devices have therefore been developed which provide pacing stimulation to one or more of the ventricles (or atria) in an attempt to improve the coordination of cardiac contractions, termed cardiac resynchronization therapy. Appropriate specification of various pacing parameters that specify the manner in which paces are delivered is necessary in order to achieve optimum improvement in cardiac function, and it is this problem with which the present invention is primarily concerned.

SUMMARY

In one of its aspects, the present invention relates to a method for optimally determining a pre-excitation timing parameter for delivering cardiac resynchronization therapy to the ventricles. The method may be performed by an implantable cardiac rhythm management device configured to deliver such therapy using data received from its sensing channels in order to effect automatic optimization of the amount of pre-excitation therapy delivered to an individual patient. In accordance with the invention, the device measures one or more intrinsic conduction parameters from electrogram signals generated during intrinsic beats. The pre-excitation timing parameter is then set automatically in accordance with a formula that includes a linear combination of the measured intrinsic conduction parameters as defined by a set of specified coefficients. The specified coefficients may be pre-derived from a linear regression analysis of clinical population data relating particular values of the measured intrinsic conduction parameters to an optimum value of the pre-excitation timing parameter as determined by concurrent measurement of another parameter reflective of cardiac function. An example of a pre-excitation timing parameter that may be automatically set by the device in this manner is the atrio-ventricular delay used in atrial-tracking or AV sequential pacing of the ventricles.

DETAILED DESCRIPTION

Applying cardiac resynchronization therapy in the most efficacious manner requires optimal selection of a number of pacing parameters. Described below is a cardiac rhythm management device configurable for delivering resynchronization pacing to the left ventricle (LV) and/or the right ventricle (RV) in order to compensate for ventricular conduction delays and improve the coordination of ventricular contractions. The device may be further programmed to automatically set certain pacing parameters in accordance with information gathered from its sensing channels. Among the pacing parameters which may be set in this manner are the selection of which heart chambers are to be paced, the atrio-ventricular delay interval, the biventricular stimulation delay or LV offset interval, and selection between alternative LV pacing sites.

1. Exemplary Device Description

Conventional cardiac pacing with implanted pacemakers involves excitatory electrical stimulation of the heart by the delivery of pacing pulses to an electrode in electrical contact with the myocardium. The pacemaker is usually implanted subcutaneously on the patient's chest, and is connected to electrodes by leads threaded through the vessels of the upper venous system into the heart. An electrode can be incorporated into a sensing channel that generates an electrogram signal representing cardiac electrical activity at the electrode site and/or incorporated into a pacing channel for delivering pacing pulses to the site.

Figure 1:
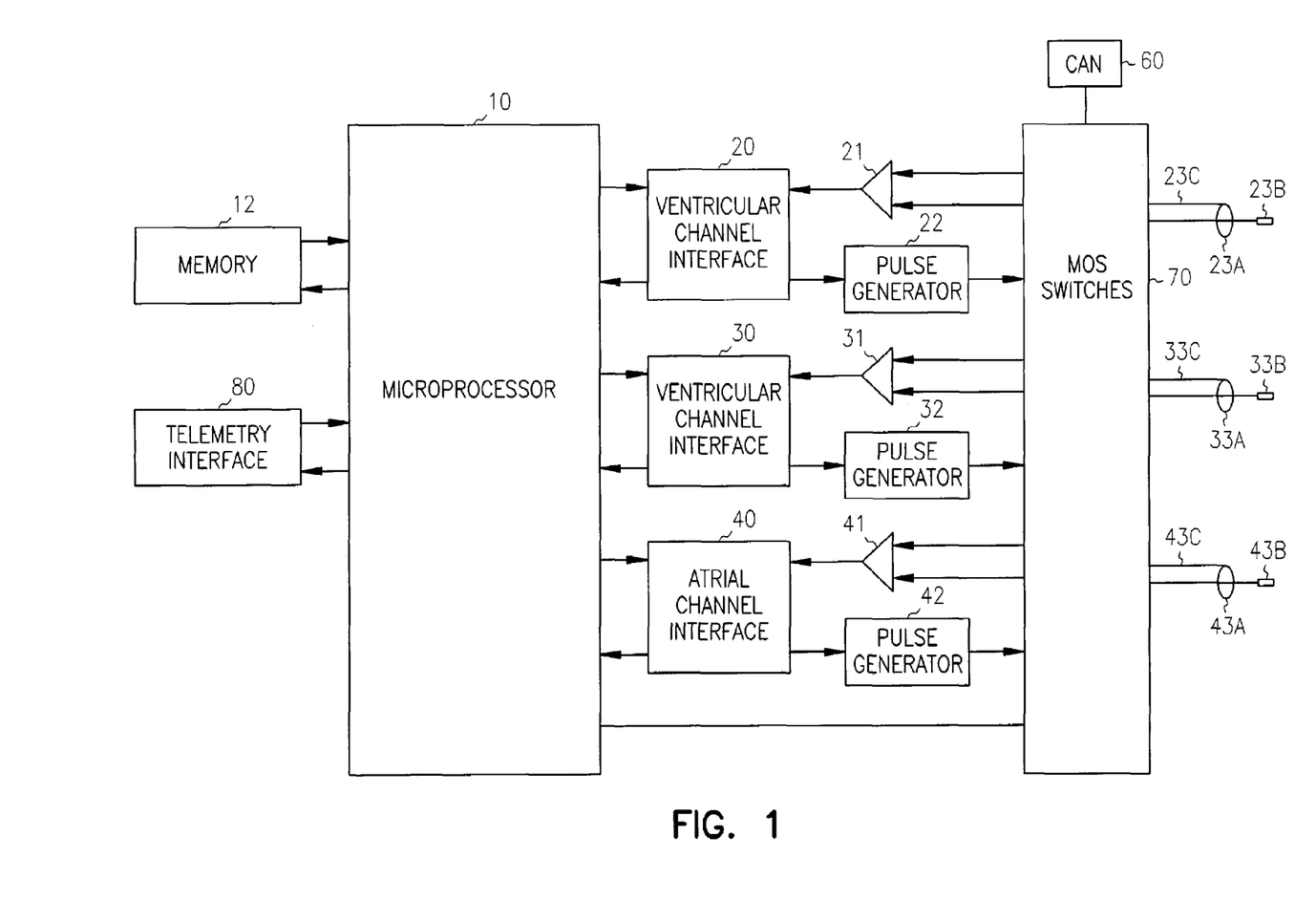
FIG. 1 is a block diagram of an exemplary cardiac device for practicing the present invention.

A block diagram of a multi-site pacemaker having multiple sensing and pacing channels is shown in FIG. 1. (As the term is used herein, a "pacemaker" should be taken to mean any cardiac rhythm management device, such as an implantable cardioverter/defibrillator, with a pacing functionality.)

The controller of the pacemaker is made up of a microprocessor 10 communicating with a memory 12 via a bidirectional data bus, where the memory 12 typically comprises a ROM (read-only memory) for program storage and a RAM (random-access memory) for data storage. The controller could be implemented by other types of logic circuitry (e.g., discrete components or programmable logic arrays) using a state machine type of design, but a microprocessor-based system is preferable. As used herein, the programming of a controller should be taken to refer to either discrete logic circuitry configured to perform particular functions or to the code executed by a microprocessor. The controller is capable of operating the pacemaker in a number of programmed modes where a programmed mode defines how pacing pulses are output in response to sensed events and expiration of time intervals. A telemetry interface 80 is also provided for communicating with an external programmer.

The embodiment shown in FIG. 1 has three sensing/pacing channels, where a pacing channel is made up of a pulse generator connected to an electrode while a sensing channel is made up of the sense amplifier connected to an electrode. A MOS switching network 70 controlled by the microprocessor is used to switch the electrodes from the input of a sense amplifier to the output of a pulse generator. The switching network 70 also allows the sensing and pacing channels to be configured by the controller with different combinations of the available electrodes. The channels may be configured as either atrial or ventricular channels allowing the device to deliver conventional ventricular single-site pacing with or without atrial tracking, biventricular pacing, or multi-site pacing of a single chamber. In an example configuration, a right atrial sensing/pacing channel includes ring electrode 43a and tip electrode 43b of bipolar lead 43c, sense amplifier 41, pulse generator 42, and a channel interface 40. A right ventricular sensing/pacing channel includes ring electrode 23a and tip electrode 23b of bipolar lead 23c, sense amplifier 21, pulse generator 22, and a channel interface 20, and a left ventricular sensing/pacing channel includes ring electrode 33a and tip electrode 33b of bipolar lead 33c, sense amplifier 31, pulse generator 32, and a channel interface 30. The channel interfaces communicate bi-directionally with a port of microprocessor 10 and include analog-to-digital converters for digitizing sensing signal inputs from the sensing amplifiers, registers that can be written to for adjusting the gain and threshold values of the sensing amplifiers, and registers for controlling the output of pacing pulses and/or changing the pacing pulse amplitude. In this embodiment, the device is equipped with bipolar leads that include two electrodes which are used for outputting a pacing pulse and/or sensing intrinsic activity. Other embodiments may employ unipolar leads with single electrodes for sensing and pacing. The switching network 70 may configure a channel for unipolar sensing or pacing by referencing an electrode of a unipolar or bipolar lead with the device housing or can 60.

The controller 10 controls the overall operation of the device in accordance with programmed instructions stored in memory. The controller 10 interprets electrogram signals from the sensing channels and controls the delivery of paces in accordance with a pacing mode. The sensing circuitry of the pacemaker generates atrial and ventricular electrogram signals from the voltages sensed by the electrodes of a particular channel. When an electrogram signal in an atrial or ventricular sensing channel exceeds a specified threshold, the controller detects an atrial or ventricular sense, respectively, which pacing algorithms may employ to trigger or inhibit pacing. An electrogram is analogous to a surface ECG and indicates the time course and amplitude of cardiac depolarization that occurs during either an intrinsic or paced beat.

2. Cardiac Resynchronization Pacing Therapy

Cardiac resynchronization therapy is most conveniently delivered in conjunction with a bradycardia pacing mode. Bradycardia pacing modes refer to pacing algorithms used to pace the atria and/or ventricles in a manner that enforces a certain minimum heart rate. Because of the risk of inducing an arrhythmia with asynchronous pacing, most pacemakers for treating bradycardia are programmed to operate synchronously in a so-called demand mode where sensed cardiac events occurring within a defined interval either trigger or inhibit a pacing pulse. Inhibited demand pacing modes utilize escape intervals to control pacing in accordance with sensed intrinsic activity. In an inhibited demand mode, a pacing pulse is delivered to a heart chamber during a cardiac cycle only after expiration of a defined escape interval during which no intrinsic beat by the chamber is detected. For example, a ventricular escape interval for pacing the ventricles can be defined between ventricular events, referred to as the VV interval with its inverse being the lower rate limit or LRL. The VV interval is restarted with each ventricular sense or pace. In atrial tracking and AV sequential pacing modes, another ventricular escape interval is defined between atrial and ventricular events, referred to as the atrio-ventricular pacing delay interval or AVD, where a ventricular pacing pulse is delivered upon expiration of the atrio-ventricular pacing delay interval if no ventricular sense occurs before. In an atrial tracking mode, the atrio-ventricular pacing delay interval is triggered by an atrial sense and stopped by a ventricular sense or pace. An atrial escape interval can also be defined for pacing the atria either alone or in addition to pacing the ventricles. In an AV sequential pacing mode, the atrio-ventricular delay interval is triggered by an atrial pace and stopped by a ventricular sense or pace. Atrial tracking and AV sequential pacing are commonly combined so that the AVD starts with either an atrial pace or sense.

As described above, cardiac resynchronization therapy is pacing stimulation applied to one or more heart chambers in a manner that compensates for conduction delays. Ventricular resynchronization pacing is useful in treating heart failure in patients with interventricular or intraventricular conduction defects because, although not directly inotropic, resynchronization results in a more coordinated contraction of the ventricles with improved pumping efficiency and increased cardiac output. Ventricular resynchronization can be achieved in certain patients by pacing at a single unconventional site, such as the left ventricle instead of the right ventricle in patients with left ventricular conduction defects. Resynchronization pacing may also involve biventricular pacing, either simultaneously or non-simultaneously. The latter may be termed biventricular offset pacing. The offset interval may be zero in order to pace both ventricles simultaneously, positive in order to pace the left after the right, or negative to pace the left before the right.

Cardiac resynchronization therapy is most commonly applied in the treatment of patients with heart failure due to left ventricular dysfunction which is either caused by or contributed to by ventricular conduction abnormalities. In such patients, the left ventricle or parts of the left ventricle contract later than normal during systole which thereby impairs pumping efficiency. In order to resynchronize ventricular contractions in such patients, pacing therapy is applied such that the left ventricle or a portion of the left ventricle is pre-excited relative to when it would become depolarized in an intrinsic contraction. Optimal pre-excitation in a given patient may be obtained with biventricular offset pacing where the left ventricle is paced before, after, or simultaneously with the right ventricle, or with left ventricular-only pacing.

Once a particular resynchronization pacing mode is selected for a patient, pacing parameters affecting the manner and extent to which pre-excitation is applied must be specified. Such pre-excitation timing parameters would include, for example, the atrio-ventricular pacing delay interval and the biventricular or left ventricular offset interval. The biventricular and left ventricular offset intervals determine the manner in which the left ventricle is pre-excited relative to right ventricular events. The length of the specified AVD relative to the intrinsic atrio-ventricular delay dictates the extent of pacing stimulation delivered to the ventricle and, therefore, the amount of pre-excitation delivered to the patient. In order to optimally specify these parameters, the patient may be subjected to clinical testing after implantation where the parameters are varied as cardiac function is assessed. For example, a patient may be given resynchronization stimulation while varying pre-excitation timing parameters in order to determine the values of the parameters that result in maximum cardiac performance, as determined by measuring a parameter reflective of cardiac function such as maximum left ventricular pressure change (dP/dt).

3. Automatic Setting of Pre-Excitation Timing Parameters

Since the optimum values for the pre-excitation timing parameters discussed above vary not only from patient to patient but may also change over time in an individual patient, it would be desirable for a cardiac resynchronization device to possess a means of automatically determining those optimum values. One method that could be used in atrial tracking modes where the patient has a normal sinus rhythm is for the device to adjust the atrio-ventricular pacing delay interval and/or biventricular offset interval to values that result in the slowest intrinsic atrial rate. The body's baroreceptor feedback mechanism for regulating heart rate is thus used as a surrogate measure of cardiac output. This method, however, requires running a lengthy pacing protocol and can only be applied in patients with intact pathways for regulating heart rate and only in pacing modes where the atria are not paced.

In the approach of the present invention, an implantable cardiac resynchronization device is programmed to measure one or more intrinsic conduction parameters from electrogram signals generated during intrinsic beats. The measured intrinsic conduction parameters may represent averages of values obtained during a specified number of intrinsic beats. The device then automatically sets a pre-excitation timing parameter such as the AVD or biventricular offset interval in accordance with a formula that equates an optimum value of the pre-excitation timing parameter to a linear sum of the measured intrinsic conduction parameters multiplied by specified coefficients. In order to pre-derive the specified coefficients for later programming into the device, clinical population data is obtained that relates particular values of the measured intrinsic conduction parameters to an optimum value of the pre-excitation timing parameter as determined by concurrent measurement of another parameter reflective of cardiac function (e.g., maximum dP/dt or minimum atrial rate). A linear regression analysis is then performed to derive values of the specified coefficients used in the formula for setting the pre-excitation timing parameter, the specified coefficients thus being regression coefficients.

The AVD interval determines the amount of pre-excitation delivered by resynchronization, and its optimum value in any particular patient depends on the intrinsic atrio-ventricular interval and the degree of the patient's conduction pathology. The latter is related to the duration of ventricular depolarization during an intrinsic contraction as reflected by the QRS width in a surface electrocardiogram. The intrinsic left ventricular depolarization duration can also be determined from intra-cardiac electrograms such as are generated in the device's sensing channels. The device may therefore be programmed to measure these intrinsic conduction parameters from electrogram signals and use them in the formula obtained by linear regression as described above to optimally set the AVD.

Figure 2:
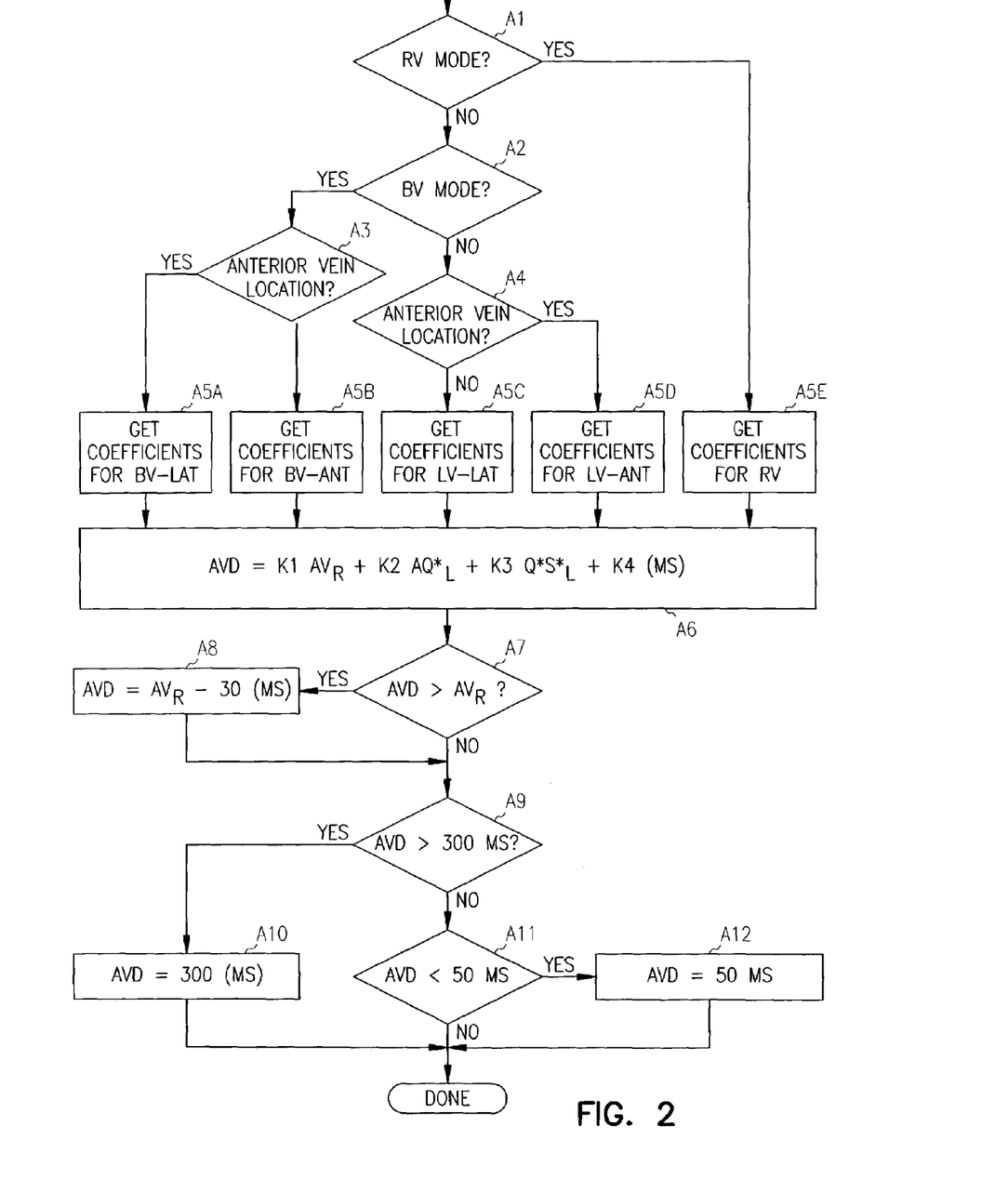
FIG. 2 illustrates an exemplary algorithm for calculating the atrio-ventricular delay interval used in atrial-tracking and AV sequential pacing modes.

FIG. 2 illustrates an exemplary implementation of the above-described method for automatically setting the AVD as could be executed by an appropriately programmed implantable cardiac device. In this embodiment, the optimum AVD is set according to the following formula:

$$AVD = k_1 AV_R + k_2 AQ^*_L + k_3 Q^*S^* + k_4$$

where $AV_R$ is the right intrinsic atrio-ventricular delay measured as the interval between an atrial sense and a right ventricular sense, $AQ^*_L$ is the left intrinsic atrio-ventricular delay measured as the interval between an atrial sense and the start of left ventricular depolarization in an electrogram, and $Q^*S^*$ is the duration of ventricular depolarization is measured as the interval from the start of left ventricular depolarization to the end of left ventricular depolarization in an electrogram. The start and end of depolarization may be detected by the device from an electrogram using a threshold criterion similar to that used for detecting chamber senses. The specified coefficients are $k_1$, $k_2$, $k_3$, and $k_4$, where different sets of coefficients are used depending upon which chambers are paced in the currently programmed mode and the location of the left ventricular pacing lead. Each set of specified coefficients may derived by a regression analysis of clinical data relating the optimum AVD to the measured intrinsic conduction parameters using a pacing mode for pacing a particular chamber or chambers and using a particular location for the left ventricular pacing lead.

Referring to FIG. 2, the device determines at steps A1 and A2 whether it is operating in a right ventricular-only pacing mode (RV mode), biventricular pacing mode (BV mode), or left ventricular-only pacing mode (LV mode). If in RV mode, specified coefficients for optimum setting of the AVD interval in that mode are obtained at step A5e. If in BV mode, the device determines at step A3 whether the left ventricular pacing lead is in an anterior or lateral ventricular location, the latter corresponding to the left ventricular free wall. If the left ventricular pacing lead is lateral, specified coefficients for optimum setting of the AVD in that situation are obtained at step A5a, while if the left ventricular pacing lead is anterior, specified coefficients for optimum setting of the AVD are obtained at step A5b. Similarly, if it is determined at step A2 that the device is operating in LV mode, the left ventricular pacing lead location is determined at step A4 so that specified coefficients for setting the AVD are obtained at either step A5c or A5d in accordance with whether the left ventricular pacing lead location is lateral or anterior, respectively. The calculated AVD value is next compared with the right intrinsic atrio-ventricular delay at step A7. If the calculated AVD value is greater than the right intrinsic atrio-ventricular delay, the AVD is set to the value of the latter plus a specified margin (in this case, 30 ms). At steps A9 through A12, the calculated AVD is compared with specified maximum and minimum limit values (300 and 50 ms, respectively, in this case). If the calculated AVD exceeds the maximum limit value, the AVD is set to the maximum limit value. If the calculated AVD is below the minimum limit value, the AVD is set to the minimum limit value. In an alternative embodiment, if the calculated AVD value is greater than the minimum of a fixed percentage of the right intrinsic atrio-ventricular delay (e.g., 70%) or a fixed value (e.g., 300 ms), the AVD is set to the shorter of the two values (i.e., either the fixed percentage of the intrinsic AV delay or the fixed value) or set to a minimum limit value if the calculated AVD is less than the minimum limit value.

Alternative formulas for calculating the AVD using different intrinsic conduction parameters may also be employed, examples of which are:

$$AVD = k_1 AV_R + k_2 AV_L + k_3 Q^*S^* + k_4$$

$$AVD = k_1 AV_R + k_2 Q^*S^* + k_3$$

$$AVD = k_1 AV_L + k_2 AV_R + k_3$$

$$AVD = k_1 AV_R + k_2 QRS + k_3$$

where $AV_L$ is the left intrinsic atrio-ventricular delay measured as the interval between an atrial sense and a left ventricular sense, and QRS is the width of the QRS complex as determined from a surface electrocardiogram. Which formula would produce the best results in a given situation would depend upon both the individual patient and the particular implanted device. Tables 1 through 3 show example values of specified coefficients for calculating the AVD interval using three of the different formulas discussed above. The coefficients for each formula were calculated by a linear regression analysis of data obtained from a particular clinical population relating the optimum AVD to the intrinsic conduction parameters of the formula. In the tables, the suffix appended to the pacing mode denotes the left ventricular pacing site, either anterior (Ant) or the lateral free wall (Fwl).

TABLE 1

| (AVD = k1 · $AVI_L$ + k2 · $AVI_R$ + k3) | | |
|---|---|---|
| k1 | k2 | k3 |
| LV-Ant | 0.163 | 0.769 | −59.6 |
| BV-Ant | 0.063 | 1.008 | −73.0 |
| LV-Fwl | −0.099 | 0.988 | −64.3 |
| BV-Fwl | −0.126 | 0.857 | −27.5 |

TABLE 2

| (AVD = k1 · QRS + k2 · $AVI_R$ + k3) | | |
|---|---|---|
| k1 | k2 | k3 |
| LV-Ant | −1.325 | 0.918 | 135.3 |
| BV-Ant | −0.835 | 1.041 | 49.0 |
| LV-Fwl | −0.459 | 0.911 | −4.3 |
| BV-Fwl | −0.728 | 0.757 | 71.3 |

TABLE 3

| (AVD = k1 · Q*S* + k2 · AQ* + k3 · $AVI_R$ + k4) | | | |
|---|---|---|---|
| k1 | k2 | k3 | k4 |
| LV-Ant | −0.677 | 0.808 | 0.273 | 67.5 |
| BV-Ant | −0.706 | 0.615 | 0.610 | 47.2 |
| LV-Fwl | −0.337 | 0.157 | 0.797 | −0.46 |
| BV-Fwl | −0.312 | 0.339 | 0.482 | 31.6 |

Figure 3:
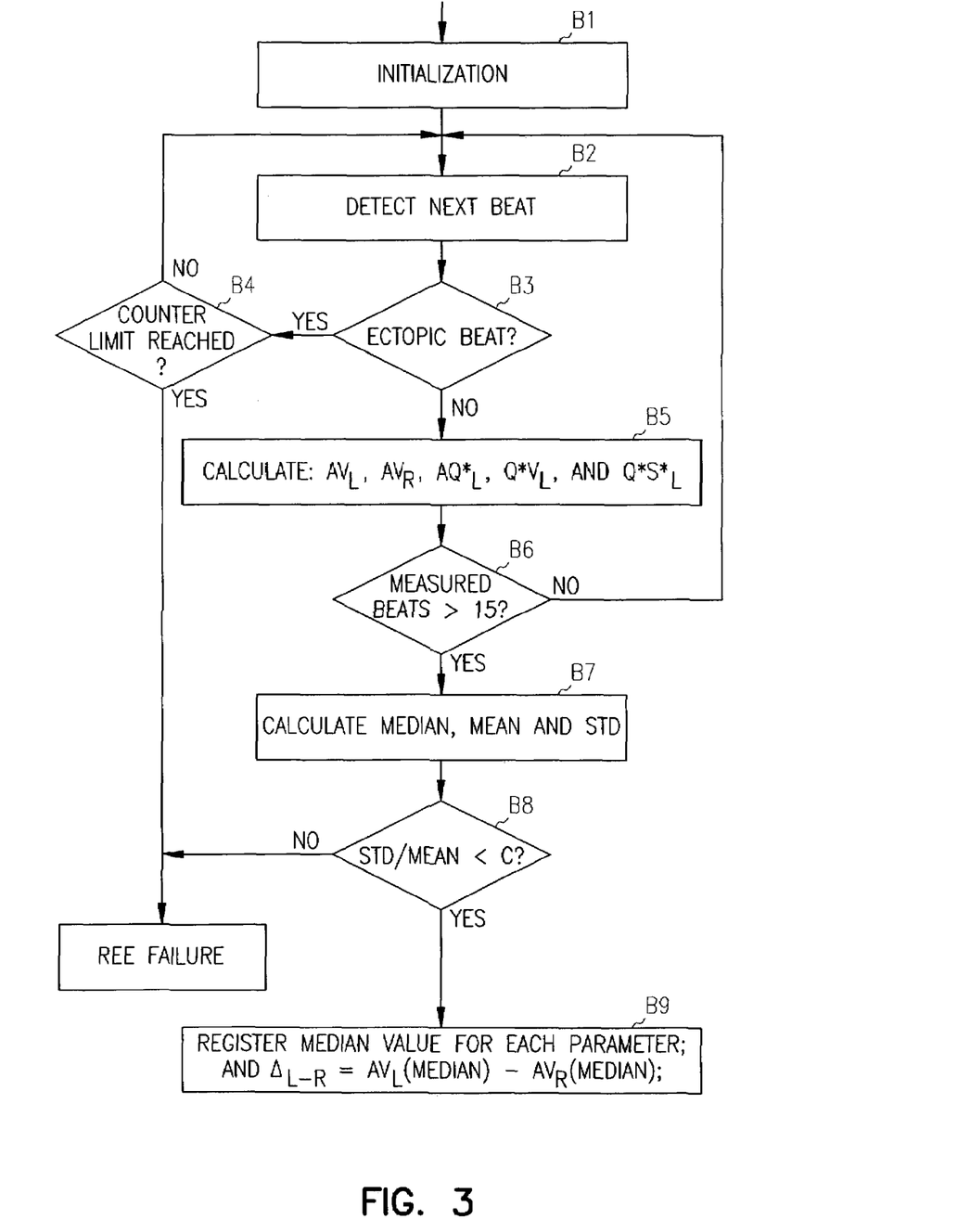
FIG. 3 illustrates an exemplary algorithm for measuring intrinsic conduction parameters.

FIG. 3 shows an exemplary algorithm for obtaining the intrinsic conduction parameters used to calculate the AVD as well as set other pacing parameters by the procedures described below. An implanted device would execute the algorithm during a data acquisition period while no pacing therapy is applied. At step B1, the sensing channels for obtaining the RV and LV electrograms are selected, and a beat counter variable is initialized. When an atrial sense occurs, a beat is detected at step B2 and the beat counter variable is incremented. If a subsequent ventricular sense does not occur, the beat is discarded as ectopic at step B3, and, if the beat counter variable does not exceed a specified limit value as tested for at step B4, the algorithm awaits the next beat detection at step B2. Otherwise the intrinsic conduction parameters $AV_L$, $AV_R$, $AQ^*_L$, $Q^*V_L$, and $Q^*S^*_L$ are measured from the RV and LV electrogram signals generated during the beat and stored at step B5. $AV_L$, $AV_R$, $AQ^*_L$, and $Q^*S^*_L$ are as defined above, and $Q^*V_L$ is the measured interval from the start of left ventricular depolarization to a left ventricular sense. At step B6, the beat counter variable is compared with another specified limit value (in this case, fifteen) and, if the limit value has not been reached, the algorithm waits for the next beat. After conduction parameters from fifteen beats have been stored, the mean, median, and standard deviation values of the parameter measurements are calculated at step B7. A step B8, the ratio of the standard deviation to the mean is calculated for all of conduction parameter measurements and compared to a specified limit value C, where in the case of $AV_L$ and $AV_R$, C=0.25, while in the case of $AQ^*_L$, $Q^*V_L$, and $Q^*S^*_L$, C=0.4. If the calculated ratios are all less than C, an average value of the stored measurement for each conduction parameter is registered and used to represent that conduction parameter at step B9. The average value of the stored measurements used in this embodiment is a median, but other embodiments may employ a mean, standard deviation, or similar statistic. In addition, an interventricular conduction delay parameter $\Delta_{L-R}$ is calculated as the difference between the average value of $AV_L$ and the average value of $AV_R$.

Figure 4:
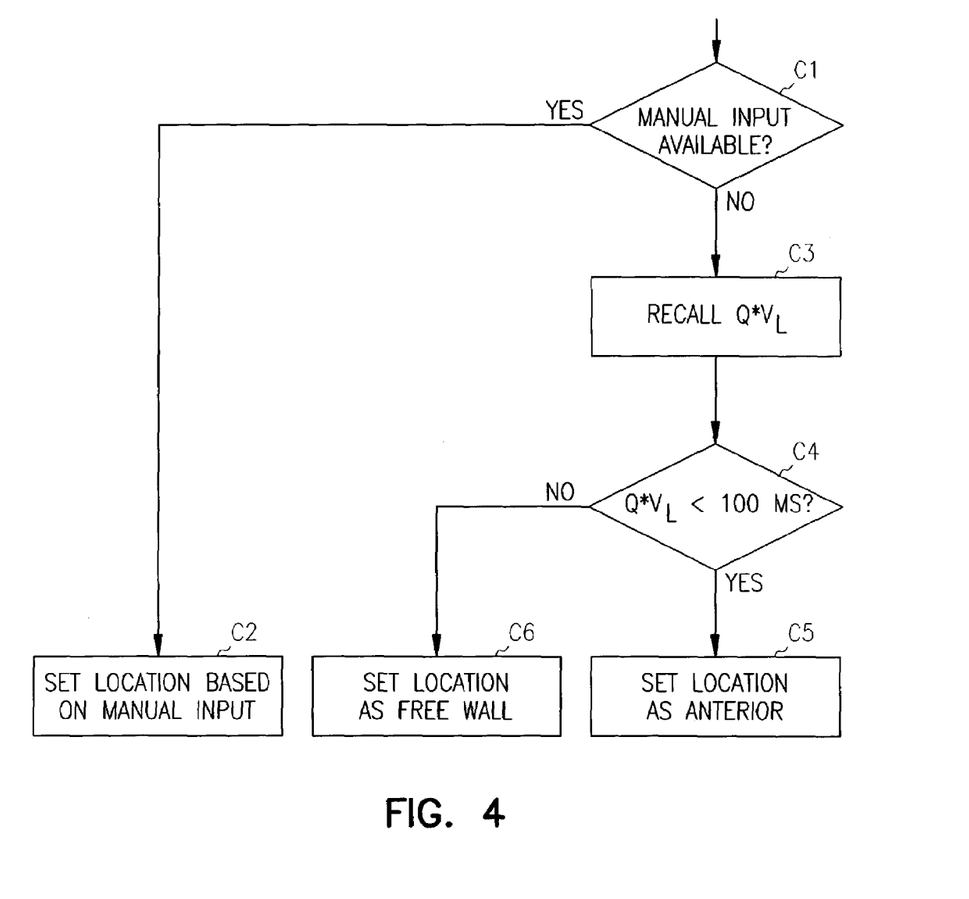
FIG. 4 illustrates an exemplary algorithm for determining the location of a left ventricular lead.

FIG. 4 illustrates an algorithm that may be executed by the controller in order to determine the left ventricular lead location, which information is used by the algorithm for calculating the AVD illustrated in FIG. 2 If manual input of the parameter is available, as determined at step C1, the algorithm sets the lead location according to the manual input at step C2. Otherwise, the representative value of the $Q^*V_L$ parameter is recalled at step C3 and compared with a limit value (in this case, 100 ms) at step C4. If the $Q^*V_L$ parameter is less than the limit value, the lead location is set as anterior at step C5. Otherwise, the lead location is set as the left ventricular free wall at step C6.

4. Automatic Configuration of Other Pacing Parameters

An implantable cardiac resynchronization device may also use measured intrinsic conduction parameters to automatically set other pacing parameters for optimal delivery of therapy. Such parameters may include which heart chambers are to be paced and which between alternative LV pacing sites should be used to pace the left ventricle.

The left ventricular lead used for sensing and pacing may be a bipolar or multi-polar lead, which thus makes available to the device alternative sites for delivering paces to the left ventricle. The selection between alternative LV pacing sites for optimal delivery of resynchronization therapy can be made based upon the relative intrinsic AV conduction delays measured from the different sites. Under most circumstances, it is desirable to pre-excite the left ventricular region that suffers the most conduction delay during an intrinsic contraction in order to compensate for that delay. For example, if two LV pacing sites L1 and L2 are available, the intrinsic conduction parameters $AV_{L1}$ and $AV_{LV2}$ can be measured which are the intervals between an atrial sense and a left ventricular sense detected from electrograms generated at sites L1 and L2, respectively. The pacing site which is excited later during an intrinsic beat as reflected by a longer AV delay interval can then be selected as the LV pacing site.

Figure 5:
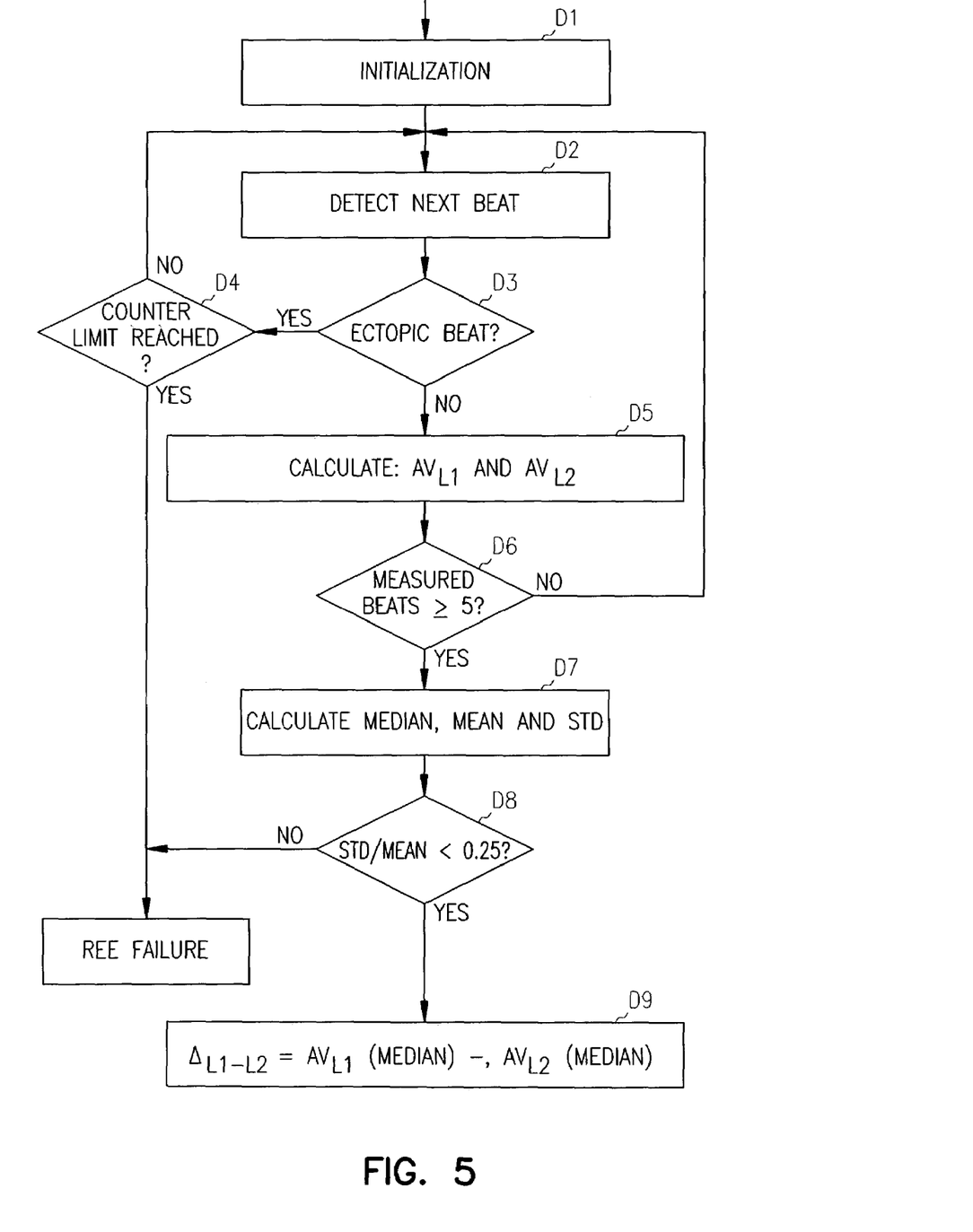
FIG. 5 illustrates an exemplary algorithm for measuring the relative intrinsic AV conduction delays at two left ventricular sites.
Figure 6:
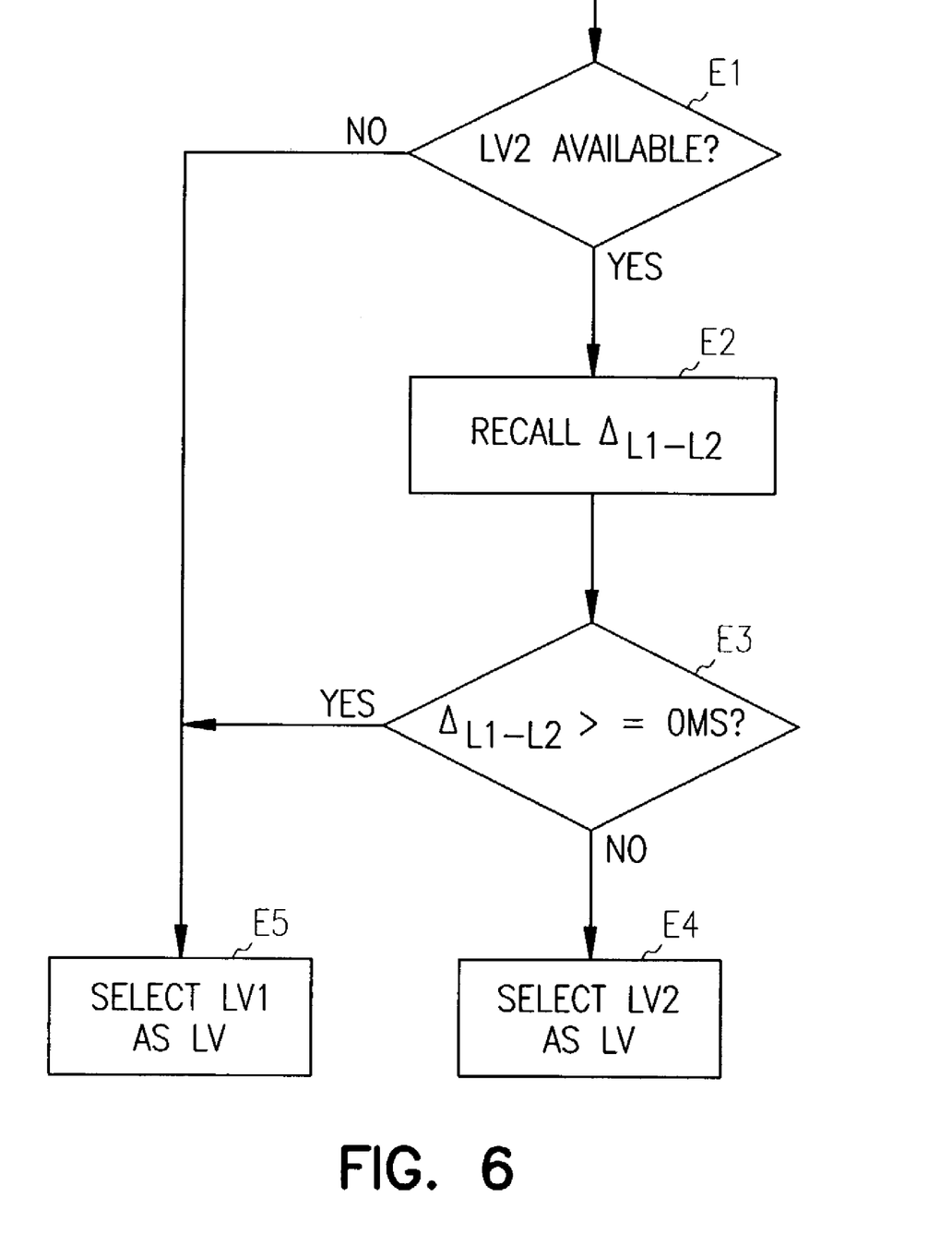
FIG. 6 illustrates an exemplary algorithm for selecting between two alternative left ventricular pacing sites.

FIG. 5 illustrates an exemplary algorithm for obtaining the $AV_{L1}$ and $AV_{LV2}$ parameters and calculating their difference, designated as $\Delta_{L1-L2}$. At step D1, the beat counter variable is reset, and the device is configured to receive electrograms from alternative sites L1 and L2. In the particular device illustrated in FIG. 1, this would involve configuring two sensing channels with electrodes at the L1 and L2 sites via the switching network 70. Steps D2 through D4 discard ectopic beats and are similar to previously described steps B2 through B4 of FIG. 3. At step D5, the conduction parameters $AV_{L1}$ and $AV_{LV2}$ are measured from the two electrograms. At step D6, the beat counter variable is compared with another specified limit value (in this case, five) and, if the limit value has not been reached, the algorithm waits for the next beat. After measurements of the parameters from five beats have been stored, the mean, median, and standard deviation values of the $AV_{L1}$ and $AV_{LV2}$ measurements are calculated at step D7. At step D8, the ratio of the standard deviation to the mean is calculated and, if found to be less than a specified limit value (in this case, 0.25), $\Delta_{L1-L2}$ is calculated as the difference between the median values of $AV_{L1}$ and $AV_{LV2}$. The device may then be programmed to select the LV pacing site in accordance with the calculated $\Delta_{L1-L2}$ parameter, an exemplary procedure for which is illustrated by FIG. 6. At step E1, the device checks if a pacing site L2 is available and, if not, selects site the default site L1 at step E5. If both sites L1 and L2 are available, the $\Delta_{L1-L2}$ parameter is recalled at step E2 and compared with zero at step E3. If $\Delta_{L1-L2}$ is negative, indicating that site L1 is excited earlier than site L2 during an intrinsic contraction, site L2 is selected as the LV pacing site at step E4. If $\Delta_{L1-L2}$ is greater than or equal to zero, indicating that site L1 is excited later than site L2 or at the same time, site L1 is selected as the LV pacing site at step E5.

Figure 7:
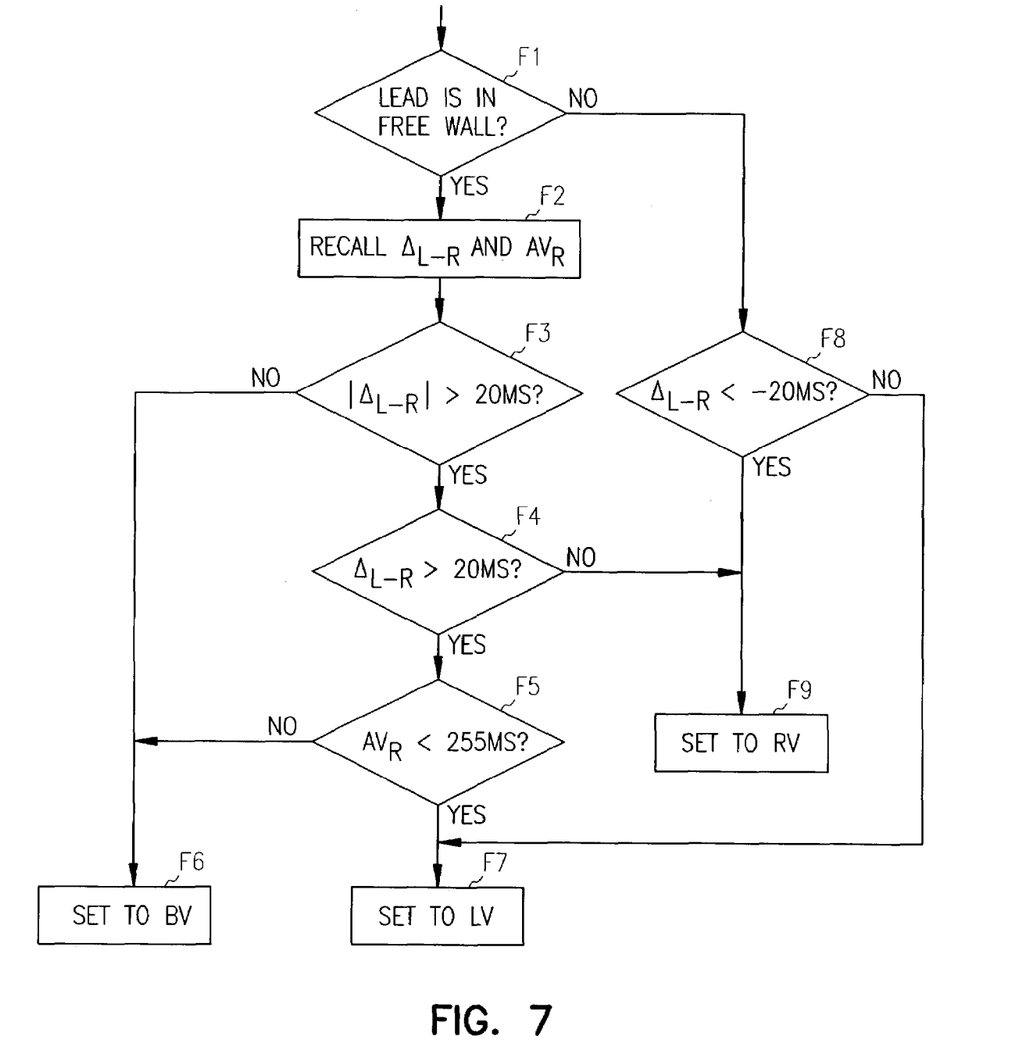
FIG. 7 illustrates an exemplary algorithm for selecting which chambers are to be paced for delivering cardiac resynchronization therapy.

The device may also be programmed to automatically select which chambers are to be paced in delivering ventricular resynchronization based upon measured intrinsic conduction parameters, an exemplary algorithm for which is illustrated in FIG. 7. At step F1, the device checks whether the left ventricular lead is located in the free wall. If so, $\Delta_{L-R}$ and $AV_R$ are recalled at step F2. If the absolute value of $\Delta_{L-R}$ is determined to be greater than 20 ms at step F3, then the device selects biventricular pacing at step F6. Otherwise, it is determined whether $\Delta_{L-R}$ exceeds 20 ms at step F4. If not, the device selects right ventricular pacing at step F9. Otherwise, it is determined whether $AV_R$ is less than 255 ms at step F5. If so, the device selects left-ventricular pacing at step F7 or, if not, selects biventricular pacing at step F6. If it is determined at step F1 that the left ventricular lead is not in the free wall, $\Delta_{L-R}$ is compared with −20 ms at step F8. If $\Delta_{L-R}$ is greater, the device selects left ventricular pacing at step F7. Otherwise, right ventricular pacing is selected at step F9.

The above-described algorithms may thus be used by an implantable cardiac device in order to automatically set pacing parameters for the optimal delivery of resynchronization therapy. One or more of the algorithms may be executed by the device controller in order to initialize the parameters prior to delivering resynchronization therapy and/or executed periodically in order to update the parameters. In an exemplary embodiment, an implantable cardiac rhythm management device would include sensing channels for generating electrogram signals corresponding to electrical activity in an atrium and both the right and left ventricles, right and left ventricular pacing channels for delivering pacing pulses to the right and left ventricles, and a controller for controlling the output of pacing pulses and interpreting electrogram signals, where the controller is programmed to pace at least one ventricle in a manner defined by at least one pre-excitation timing parameter and to measure a plurality of intrinsic conduction parameters during an intrinsic beat from electrogram signals generated in the sensing channels, including an intrinsic atrio-ventricular delay interval in each ventricular sensing channel and a duration of ventricular depolarization. The controller may then be further programmed to select between a biventricular, right ventricular-only, or left ventricular-only pacing mode based upon the measured intrinsic conduction parameters and/or set the value of the pre-excitation timing parameter according to a formula which includes a linear combination of the measured intrinsic conduction parameters as defined by specified coefficients. The pre-excitation timing parameter may be the AVD and/or an offset interval for delivering biventricular or left ventricular-only pacing. The controller may be further programmed to select between a biventricular, right ventricular-only, or left ventricular-only pacing mode based upon the measured intrinsic conduction parameters and a specified location of a left ventricular lead used by the left ventricular sensing and pacing channels, where the location of the left ventricular lead is specified by user input or determined from the value of $Q^*V_L$. The device may also be equipped with a plurality of sensing/pacing electrodes, sense amplifiers, pulse generators, and a switching network operated by the controller for configuring a sensing channel by connecting a selected electrode pair to a selected sense amplifier and for configuring a pacing channel by connecting a selected electrode pair to a selected pulse generator. The plurality of sensing/pacing electrodes may include at least two alternative left ventricular electrodes located at different left ventricular sites, and the measured intrinsic conduction parameters may include AV conduction delays measured from the at least two alternative left ventricular electrodes. The controller may then be programmed to select between the alternative left ventricular electrodes for configuring the left ventricular pacing channel based upon the intrinsic AV conduction delays measured from each alternative left ventricular electrode such as by configuring the left ventricular pacing channel with whichever of the alternative left ventricular electrodes has the longest intrinsic AV conduction delay measured from it.

Although the invention has been described in conjunction with the foregoing specific embodiments, many alternatives, variations, and modifications will be apparent to those of ordinary skill in the art. Other such alternatives, variations, and modifications are intended to fall within the scope of the following appended claims.

What is claimed is:

1. A cardiac rhythm management device, comprising:
an atrial sensing channel for generating electrogram signals corresponding to electrical activity in an atrium;
right and left ventricular sensing channels for generating electrogram signals corresponding to electrical activity in the right and left ventricles, respectively;
right and left ventricular pacing channels for delivering pacing pulses to the right and left ventricles, respectively;
a controller for controlling the output of pacing pulses and interpreting electrogram signals, wherein the controller is programmed to pace at least one ventricle within a programmable atrio-ventricular delay (AVD) interval after an atrial sense in an atrial-tracking mode;
wherein the controller is programmed to include instructions to perform:
measure at least one intrinsic atrio-ventricular delay interval and a duration of ventricular depolarization from electrogram signals during an intrinsic beat; and
set the AVD interval according to a formula which includes a linear combination of the measured intrinsic atrio-ventricular delay and the measured duration of ventricular depolarization defined by specified coefficients.

2. The device of claim 1 wherein the measured intrinsic atrio-ventricular delay and the measured duration of ventricular depolarization each represent averages, the controller being programmed to measure an intrinsic atrio-ventricular delay interval and a duration of ventricular depolarization during a specified number of intrinsic beats and compute averages therefrom.

3. The device of claim 1 wherein the controller is programmed to measure right and left intrinsic atrio-ventricular delay intervals and wherein the formula for setting the AVD interval includes a linear combination of the measured right and left intrinsic atrio-ventricular delays and the measured duration of ventricular depolarization.

4. The device of claim 3 wherein the right intrinsic atrio-ventricular delay is measured as the interval between an atrial sense and a right ventricular sense designated as $AV_R$, the left intrinsic atrio-ventricular delay is measured as the interval between an atrial sense and the start of left ventricular depolarization in an electrogram designated as $AQ^*_L$, the duration of ventricular depolarization is measured as the interval from the start of left ventricular depolarization to the end of left ventricular depolarization in an electrogram designated as $Q^*S^*$, and the formula for setting the AVD is:

$$AVD = k_1 AV_R + k_2 AQ^*_L + k_3 Q^*S^* + k_4$$

where $k_1$, $k_2$, $k_3$, and $k_4$ are specified coefficients.

5. The device of claim 1 wherein the right intrinsic atrio-ventricular delay is measured as the interval between an atrial sense and a right ventricular sense designated as $AV_R$, the left intrinsic atrio-ventricular delay is measured as the interval between an atrial sense and a left ventricular sense designated as $AV_L$, and the formula for setting the AVD is:

$$AVD = k_1 AV_R + k_2 AV_L + k_3$$

where $k_1$, $k_2$, and $k_3$, are specified coefficients.

6. The device of claim 1 wherein the intrinsic atrio-ventricular delay is measured as the interval between an atrial sense and a right ventricular sense designated as $AV_R$, the duration of ventricular depolarization is measured as the interval from the start of left ventricular depolarization to the end of left ventricular depolarization in an electrogram designated as $Q^*S^*$, and the formula for setting the AVD is:

$$AVD = k_1 AV_R + k_2 Q^*S^* + k_3$$

where $k_1$, $k_2$, and $k_3$ are specified coefficients.

7. The device of claim 1 further comprising an atrial pacing channel and wherein the controller is further programmed to pace at least one ventricle within the programmable atrio-ventricular delay (AVD) interval after an atrial pace in an AV sequential pacing mode.

8. The device of claim 1 wherein the specified coefficients defining the linear combination of the measured intrinsic atrio-ventricular delay interval and the measured duration of ventricular depolarization have been pre-derived from a linear regression analysis of clinical population data relating measured intrinsic atrio-ventricular delay intervals and measured durations of ventricular depolarization to an optimum AVD for delivering cardiac resynchronization therapy as determined by measurement of a cardiac function parameter.

9. The device of claim 1 wherein the controller is programmed to select different sets of specified coefficients defining the linear combination of the measured intrinsic atrio-ventricular delay interval and the measured duration of ventricular depolarization used to set the AVD in accordance with whether the controller is programmed to deliver pacing pulses in a left-ventricular, biventricular, or right-ventricular pacing mode.

10. The device of claim 9 wherein the controller is programmed to select different sets of specified coefficients defining the linear combination of the measured intrinsic atrio-ventricular delay intervals and the measured duration of ventricular depolarization used to set the AVD in accordance with the location of a left ventricular lead used to deliver pacing pulses by the left ventricular pacing channel.

11. The device of claim 10 wherein the controller is programmed to measure the interval from the start of left ventricular depolarization to a left ventricular sense, designated as $Q^*V_L$, and determine the location of the left ventricular lead based upon the value of $Q^*V_L$.

12. A method for operating a cardiac rhythm management device, comprising:
generating electrogram signals corresponding to electrical activity in an atrium and the right and left ventricles;
pacing at least one ventricle within a programmable atrio-ventricular delay (AVD) interval after an atrial sense in an atrial-tracking mode;
measuring an intrinsic atrio-ventricular delay interval and a duration of ventricular depolarization from electrogram signals during an intrinsic beat; and
setting the AVD interval according to a formula which includes a linear combination of the measured intrinsic atrio-ventricular delay and the measured duration of ventricular depolarization defined by specified coefficients.

13. The method of claim 12 further comprising taking measurements of the intrinsic atrio-ventricular delay interval and duration of ventricular depolarization during a specified number of intrinsic beats and computing averages of those measurements such that the measured intrinsic atrio-ventricular delay and the measured duration of ventricular depolarization each represent average values.

14. The method of claim 12 further comprising measuring right and left intrinsic atrio-ventricular delay intervals and wherein the formula for setting the AVD interval includes a linear combination of the measured right and left intrinsic atrio-ventricular delays and the measured duration of ventricular depolarization.

15. The method of claim 14 wherein the right intrinsic atrio-ventricular delay is measured as the interval between an atrial sense and a right ventricular sense designated as $AV_R$, the left intrinsic atrio-ventricular delay is measured as the interval between an atrial sense and a left ventricular sense designated as $AV_L$, and the formula for setting the AVD is:

$$AVD=k_1AV_R+k_2AV_L+k_3$$

where $k_1$, $k_2$, and $k_3$, are specified coefficients.

16. The method of claim 14 wherein the right intrinsic atrio-ventricular delay is measured as the interval between an atrial sense and a right ventricular sense designated as $AV_R$, the left intrinsic atrio-ventricular delay is measured as the interval between an atrial sense and the start of left ventricular depolarization in an electrogram designated as $AQ^*_L$, the duration of ventricular depolarization is measured as the interval from the start of left ventricular depolarization to the end of left ventricular depolarization in an electrogram designated as $Q^*S^*$, and the formula for setting the AVD is:

$$AVD=k_1AV_R+k_2AQ^*_L+k_3Q^*S^*+k_4$$

where $k_1$, $k_2$, $k_3$, and $k_4$ are specified coefficients.

17. The method of claim 12 wherein the intrinsic atrio-ventricular delay is measured as the interval between an atrial sense and a right ventricular sense designated as $AV_R$, the duration of ventricular depolarization is measured as the interval from the start of left ventricular depolarization to the end of left ventricular depolarization in an electrogram designated as $Q^*S^*$, and the formula for setting the AVD is:

$$AVD=k_1AV_R+k_2Q^*S^*+k_3$$

where $k_1$, $k_2$, and $k_3$ are specified coefficients.

18. The method of claim 12 wherein the specified coefficients defining the linear combination of the measured intrinsic atrio-ventricular delay and the measured duration of ventricular depolarization have been pre-derived from a linear regression analysis of clinical population data relating measured intrinsic atrio-ventricular delay intervals and measured durations of ventricular depolarization to an optimum AVD for delivering cardiac resynchronization therapy as determined by measurement of a cardiac function parameter.

19. The method of claim 12 further comprising selecting different sets of specified coefficients defining the linear combination of the measured intrinsic atrio-ventricular delay and the measured duration of ventricular depolarization used to set the AVD in accordance with whether the device is programmed to deliver pacing pulses in a left-ventricular, biventricular, or right-ventricular pacing mode.

20. The method of claim 12 further comprising selecting different sets of specified coefficients defining the linear combination of the measured intrinsic atrio-ventricular delay and the measured duration of ventricular depolarization used to set the AVD in accordance with the location of a left ventricular lead used to deliver pacing pulses by the left ventricular pacing channel.

21. The method of claim 12 wherein the intrinsic atrio-ventricular delay is measured as the interval between an atrial sense and a right ventricular sense designated as $AV_R$, the duration of ventricular depolarization is measured as the duration of a QRS complex in a surface EKG, and the formula for setting the AVD is:

$$AVD=k_1AV_R+k_2QRS+k_3$$

where $k_1$, $k_2$, and $k_3$ are specified coefficients.

22. A cardiac rhythm management device, comprising:
an atrial sensing channel for generating electrogram signals corresponding to electrical activity in an atrium;
right and left ventricular sensing channels for generating electrogram signals corresponding to electrical activity in the right and left ventricles, respectively;
right and left ventricular pacing channels for delivering pacing pulses to the right and left ventricles, respectively;
a controller for controlling the output of pacing pulses and interpreting electrogram signals, wherein the controller is programmed to pace at least one ventricle in a manner defined by at least one pre-excitation timing parameter;
wherein the controller is programmed to include instructions to perform:
measure a plurality of intrinsic conduction parameters during an intrinsic beat from electrogram signals generated in the sensing channels, including an intrinsic atrio-ventricular delay interval in each ventricular sensing channel and a duration of ventricular depolarization;
select between a biventricular, right ventricular-only, or left ventricular-only pacing mode based upon the measured intrinsic conduction parameters;
set the value of the pre-excitation timing parameter according to a formula which includes a linear combination of the measured intrinsic conduction parameters as defined by specified coefficients.

23. The device of claim 22 wherein the specified coefficients defining the linear combination of the measured intrinsic conduction parameters for setting the value of the pre-excitation timing parameter have been pre-derived from a linear regression analysis of clinical population data relating measured intrinsic conduction parameters to an optimum pre-excitation timing parameter value for delivering cardiac resynchronization therapy as determined by measurement of a cardiac function parameter.

24. The device of claim 22 wherein the controller is programmed to pace at least one ventricle within a programmable atrio-ventricular delay (AVD) interval after atrial sense in an atrial-tracking mode, and wherein the pre-excitation timing parameter is the AVD.

25. The device of claim 22 wherein the controller is programmed to pace at least one ventricle within a programmable offset interval with respect to a pace or sense in the contralateral ventricle, and wherein the pre-excitation timing parameter is the offset interval.

26. The device of claim 22 wherein the measured intrinsic conduction parameters include right and left intrinsic atrio-ventricular delay intervals as measured from electrograms generated in the right and left ventricular sensing channels, respectively.

27. The device of claim 22 wherein the controller is programmed to select between a biventricular, right ventricular-only, or left ventricular-only pacing mode based upon the measured intrinsic conduction parameters and a specified location of a left ventricular lead used by the left ventricular sensing and pacing channels.

28. The device of claim 27 wherein the plurality of measured intrinsic conduction parameters include the interval from the start of left ventricular depolarization to a left ventricular sense, designated as $Q^*V_L$, and wherein the controller is programmed to determine a location of a left ventricular lead used by the left ventricular sensing and pacing channels from the value of $Q^*V_L$.

29. The device of claim 27 wherein the plurality of sensing/pacing electrodes includes at least two alternative left ventricular electrodes located at different left ventricular sites, wherein the measured intrinsic conduction parameters include AV conduction delays measured from the at least two alternative left ventricular electrodes, and wherein the controller is programmed to select between the alternative left ventricular electrodes for configuring the left ventricular pacing channel based upon the intrinsic AV conduction delays measured from each alternative left ventricular electrode.

30. The device of claim 29 wherein the controller is programmed to configure the left ventricular pacing channel with whichever of the alternative left ventricular electrodes has the longest intrinsic AV conduction delay measured from it.

31. The device of claim 22 further comprising:
- a plurality of sensing/pacing electrodes for disposition near selected myocardial sites;
- a plurality of sense amplifiers for amplifying an electrogram signal received from a pair of electrodes;
- at least one pulse generator for outputting pacing pulses to a pair of electrodes;
- a switching network operated by the controller for configuring a sensing channel by connecting a selected electrode pair to a selected sense amplifier and for configuring a pacing channel by connecting a selected electrode pair to a selected pulse generator.

* * * * *

UNITED STATES PATENT AND TRADEMARK OFFICE
CERTIFICATE OF CORRECTION

PATENT NO. : 7,013,176 B2  Page 1 of 1
APPLICATION NO. : 10/352780
DATED : March 14, 2006
INVENTOR(S) : Ding et al.

It is certified that error appears in the above-identified patent and that said Letters Patent is hereby corrected as shown below:

On the Title, in field (56), under "Foreign Patent Documents", in column 2, line 1, after "1/2000" insert -- A61N/1/37 --.

In column 11, line 65, in claim 5, delete "$k_3$," and insert -- $k_3$ --, therefor.

In column 13, line 14, in claim 15, delete "$k_3$," and insert -- $k_3$ --, therefor.

Signed and Sealed this

Twenty-first Day of November, 2006

JON W. DUDAS
*Director of the United States Patent and Trademark Office*